United States Patent [19]
Lim

[11] Patent Number: 5,676,680
[45] Date of Patent: Oct. 14, 1997

[54] WRENCHLESS AND ADAPTERLESS COLLET SYSTEM FOR SURGICAL BLADES

[75] Inventor: Joepert Lim, Palm Harbor, Fla.

[73] Assignee: Linvatec Corporation, Largo, Fla.

[21] Appl. No.: 786,595

[22] Filed: Jan. 21, 1997

Related U.S. Application Data

[62] Division of Ser. No. 544,627, Oct. 18, 1995.

[51] Int. Cl.$^6$ ..................................... A61B 17/32
[52] U.S. Cl. ..................... 606/176; 606/170; 606/177; 30/339
[58] Field of Search .................... 606/82, 167, 176, 606/177, 178; 30/331, 339, 344, 351, 355, 388, 392, 393, 502, 338, 337; 83/699.21

[56] References Cited

U.S. PATENT DOCUMENTS

| | | |
|---|---|---|
| 4,657,428 | 4/1987 | Wiley . |
| 4,706,386 | 11/1987 | Wiley . |
| 4,730,952 | 3/1988 | Wiley . |
| 5,263,972 | 11/1993 | Evans et al. . |
| 5,265,343 | 11/1993 | Pascaloff . |

OTHER PUBLICATIONS

Article Entitled "Command 2" Oscillating Saws, Stryker Instruments, 1992, 2 Pages.
"The Hall Blade And Bur Book", 1994 By Zimmer, 7 Pages.
"Electronic Power At Your Fingertips. The New Hall Micro E Surgical Instruments", 1990 Zimmer, Hall Surgical, 12 Pages.
Article Entitled "New Wrenchless Collet For Hall Large Bone Oscillating Saws", Jul. 22, 1991, 2 Pages.
"The Hall Micro 100 Surgery System. Your Best Approach For Foot Surgery", 1988 Hall Surgical, 9 Pages.
"The Hall Series 4 Powered Surgical Instruments, The Power Generation", 1992 Zimmer Hall Surgical, 8 Pages.
"Hall Sterile Blades", Hall Surgical, 8 Pages.
"Adaptors For Hall Surgical Large Bone Handpieces", 1994 Zimmer, 4 Pages.
"Introducing The Versipower Plus Large Bone Instrument System", 1994 Zimmer, 6 Pages.

*Primary Examiner*—Michael Buiz
*Assistant Examiner*—Patrick W. Rasche
*Attorney, Agent, or Firm*—Gene Warzecha

[57] ABSTRACT

A method and apparatus for use as a wenchless and adapterless collet system for attaching an elongated surgical cutting blade to an oscillating surgical saw. The system comprises a collet adapted to mate with a particularly shaped blade hub. The collet has a transverse clamping head attached to a longitudinally slidable, axially aligned shaft which is adapted to slide axially along the axis of the handpiece. The handpiece has an annular anchor sleeve having an annular groove proximally adjacent to the collet clamping head. The hub at the proximal end of the blade is provided with a radially inwardly extending locking flange adapted to engage the clamping head and a radially inwardly extending anchor flange adapted to engage the annular groove in the anchor sleeve. The longitudinal spacing between the hub flanges enables the hub to be received adjacent the anchor groove in an interdigitating mating of complementarily shaped surfaces.

15 Claims, 7 Drawing Sheets

WRENCHLESS AND ADAPTERLESS COLLET SYSTEM FOR SURGICAL BLADES

This is a divisional application of application Ser. No. 08/544,627, filed Oct. 18, 1995.

BACKGROUND OF THE INVENTION

1. Field of the Invention

The invention relates generally to powered surgical tissue cutting devices. More particularly, the invention relates to mechanisms for attaching tissue cutting devices to handpieces. Still more particularly, the invention relates to wrenchless collet mechanisms for attaching tissue cutting devices to powered handpieces without the need for any additional tools or adapters.

2. Description of the Prior Art

It is often necessary to use powered tissue cutting tools in order to perform surgical procedures. Such tools generally comprise a handpiece which cyclically moves a tissue cutting device such as a blade or burr in some oscillating or reciprocating manner. The handpiece generally includes a pneumatic or electric drive motor having an output shaft to which the cutting device is attached, the shaft being axially aligned with a drive axis of the handpiece. As used herein, the term "drive axis" refers to the axis of the motor output shaft through which power is delivered from the motor. The handpiece may be a "pencil" type handpiece in which the body is elongated and the drive axis is aligned with the axis of the body or a pistol-grip type of handpiece in which the drive axis is aligned in a chosen direction relative to the grip. The drive motor of the handpiece produces a driving force which reciprocates the output shaft and cutting device either longitudinally, i.e. linearly along the drive axis (like a saber saw), or arcuately in a plane perpendicular to the drive axis. Handpieces utilizing the former type of action are generally referred to as reciprocating saws while those utilizing the latter action are generally referred to as oscillating saws. In some cases an oscillating saw may transfer the oscillating drive motion so that it is cyclical within a plane parallel to the axis of the elongated body of the handpiece. A sagittal saw is a type of oscillatory saw in which the cyclical reciprocating action is in a plane aligned with the drive axis.

In all instances, numerous tissue cutting blades or burrs or other devices (all collectively referred to herein as "blades") are adapted to be secured to the handpiece via a collet mechanism which is utilized to selectively attach and release a desired blade. A variety of different cuts can be made with a single saw depending upon the shape of the blade. For oscillating saws, the blades are often in the form of a flat, elongated body having a cutting edge (e.g. teeth, abrader, etc.) at one end and a hub at the other end, the hub being shaped and adapted to fit the particular collet. Such flat blades are used to make cuts in a plane perpendicular to the drive axis. An oscillating saw may also be used for effecting cuts in a plane parallel to the handpiece axis by attaching a transverse hub to a flat blade. A crescentic blade having a curved instead of a flat body may be used for curved cuts. The body of a crescentic blade has teeth (or another cutting edge) at its distal end which follow the shape of the arcuate body so that as the blade oscillates about the axis, the teeth follow an arcuate pattern having a center of curvature on the axis. Some flat blades may have the cutting edge at an angle to the blade body to make cuts in an angled plane. Angled blades may have an axially elongated body either on or off the blade axis. That is, the proximal end of the blade body may have a transverse hub or it may simply be attached in-line with the drive axis. The resulting cut is arcuate and facing away from the axis.

Many blade collets utilize a threaded stud axially extending from the output shaft and a nut adapted to engage the stud to clamp the blade hub to the handpiece. These collets generally require the use of separate wrench to turn the clamping nut. Since it is desirable to avoid extra tools in a surgical setting, some collets eliminate the need for a separate tool by utilizing a nut (e.g. a wingnut) that can be manipulated without tools. Other collet designs utilize a spring actuated, longitudinally movable clamping head having longitudinally extending locking pins for engagement with corresponding holes in the blade hub. The clamp head in such designs is movable to place the collet into an open position for receiving a blade and into a closed position for clamping the blade between the head and a base surface. Such designs are referred to herein as "wrenchless" designs and are generally preferable to other collet mechanisms which require the use of separate tools.

Adaptation of an axially elongated blade such as a crescentic or an angled blade to an oscillating saw is achieved in some prior art devices by providing the elongated body of the blade with a transverse hub and adapting the transverse hub to mate with an in-line wrenchless collet which can also receive a flat blade hub. This enables the saw to make cuts either in a plane perpendicular to the handpiece axis, in a plane angled with respect to the axis or along a curve having its radius of curvature on the axis. However, such axially elongated blades are often subjected to lateral loading during use such that the transverse hub acts against the spring-loaded clamp head. That is, wrenchless collet mechanisms known in oscillating saws often rely on spring pressure to securely hold a blade hub between a clamping head and a base surface. During oscillatory motion any lateral forces applied to the saw blade cause the transverse hub of the blade to lift the clamping head from its closed position, thereby compromising the security of the blade attachment. Additionally, such transverse loading may induce blade vibration and adversely affect cutting performance.

Another known method of adapting angled and crescentic blades to an oscillating saw relies on providing an axially aligned shaft at the proximal end of the blade body. Such a system is utilized in the COMMAND 2 Oscillating Saw available from Stryker Instruments, 420 E. Alcott Street, Kalamazoo, Mich. 49001. This system adapts such blades for use with a conventional oscillating saw having a clamping head transverse to the axis of the handpiece, the head having a plurality of circumferentially arranged and longitudinally extending pins facing proximally (toward the handpiece body). The clamping head is supported on an axially aligned shaft and is movable into an open position in which the head is spaced from the body of the saw and a closed position in which the head is urged under spring pressure proximally against a base surface adjacent the body of the saw. Since the saw is usable with flat blades, an adapter interface is provided for use with axially elongated blades such as angled and crescentic blades. While this saw has a wrenchless collet when it is used with flat blades, the adapter required to make this saw suitable for angled and crescentic blades makes this a tool-dependent system. The adapter has a proximal end with a semi-circular flange having a plurality of radially extending slots adapted to engage the pins on the clamping head. The distal end of the adapter is provided with an axial bore adapted to receive the axial shaft proximally extending from the angled or crescentic blade and a set screw is used to secure the shaft to the adapter. This design has the same limitations as the aforementioned prior art devices since any lateral forces exerted upon the elongated angled or crescentic blade will be translated to the semi-circular flange of the adapter and will have the same effect of compromising the security of the clamping structure. Also, this design requires not only a separate tool but an additional piece which adds to equipment present during a surgical procedure.

It is accordingly an object of this invention to produce a collet system adapted to securely hold a tissue cutting device to an oscillatory saw.

It is also an object of this invention to produce a wrenchless and adapterless system for securing a surgical blade to a powered handpiece.

It is also an object of this invention to produce a wrenchless and adapter-less system for securing angled and crescentic blades to a powered handpiece.

It is yet another object of this invention to produce a system for attaching tissue cutting devices to powered handpieces without the necessity for auxiliary tools.

It is an additional object of this invention to produce a wrenchless system for securing a surgical blade to a powered handpiece so as to decrease blade vibration induced by lateral loading on the blade.

SUMMARY OF THE INVENTION

These and other objects of this invention are achieved by the preferred embodiment disclosed herein which is a system for securing an elongated surgical device to a handpiece for driving the device. The device has an axis, a proximal end, a distal end and a hub attached to the proximal end. The hub comprises a first arcuate flange transverse to the axis and subtending a first predetermined arcuate distance. The hub also has a second arcuate flange parallel to the first arcuate flange and subtending a second predetermined arcuate distance. A collet means is attached to the handpiece for receiving the hub, the collet means comprises a first flange retaining means adapted to mate with the first arcuate flange and a second flange retaining means adapted to mate with the second arcuate flange. A pressure means is used for urging the second flange retaining means into engagement with the second arcuate flange.

The invention is further embodied in an elongated surgical blade for use with a handpiece for driving the blade in a cyclical manner relative to the axis of the handpiece. The blade has an elongated member having a proximal end and a distal end. A cutting member is situated at the distal end of the elongated member and a hub is situated at the proximal end. The hub comprises a pair of arcuate flanges transversely oriented to the axis and spaced a predetermined axial distance from each other, the flanges adapted to engage said handpiece.

The invention is also presented as a method of supporting a surgical device on a handpiece adapted to oscillate the device relative to the axis of the handpiece. The method comprises the steps of providing a hub on the device for attaching the device to the handpiece and providing on the handpiece a collet means for engaging the hub. The method further comprises providing on the hub and the collet means cooperating interdigitating surfaces adapted to engage when the device is engaged with the handpiece. The surfaces extend radially and arcuately sufficiently to resist the tendency for a laterally directed force on the distal end of said device to move the proximal end of the device.

DESCRIPTION OF THE PREFERRED EMBODIMENT

Figure 1:
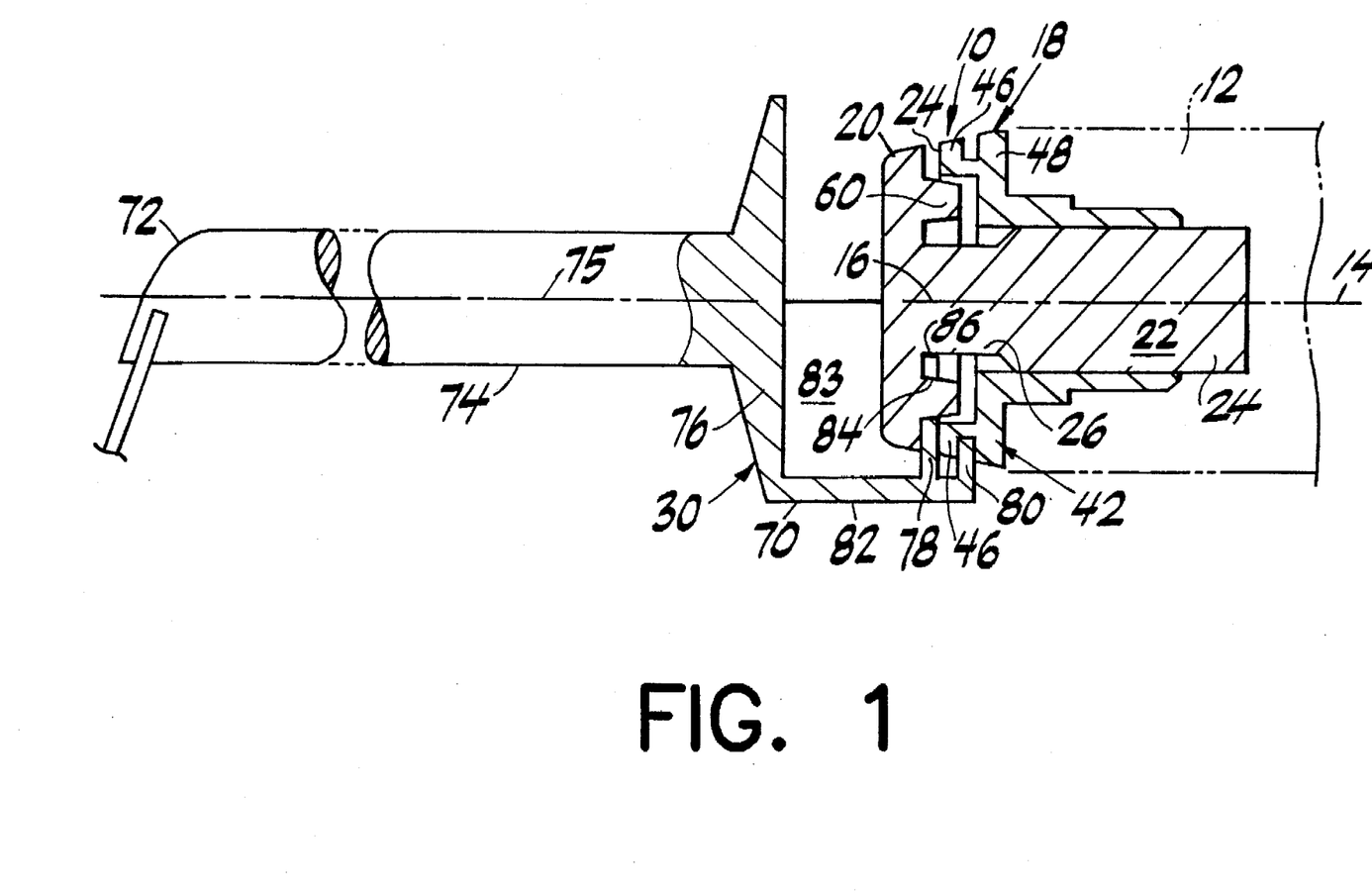
FIG. 1 is a side elevation view in cross-section of a wrenchless and adapterless collet system constructed in accordance with the principles of this invention and attached to an elongated tissue cutting device.

As shown in FIG. 1, a wrenchless collet mechanism 10 is attached to an oscillating handpiece 12 in alignment with its drive axis 14. Handpiece 12 is shown in phantom since the structure of the handpiece forms no part of the invention which is itself adaptable to a variety of different handpiece configurations. The only requirement, as will be understood below, is that the axis 16 of the collet mechanism is attached to the drive axis 14 of the handpiece such that some motion may be imparted to the collet.

Figure 2:
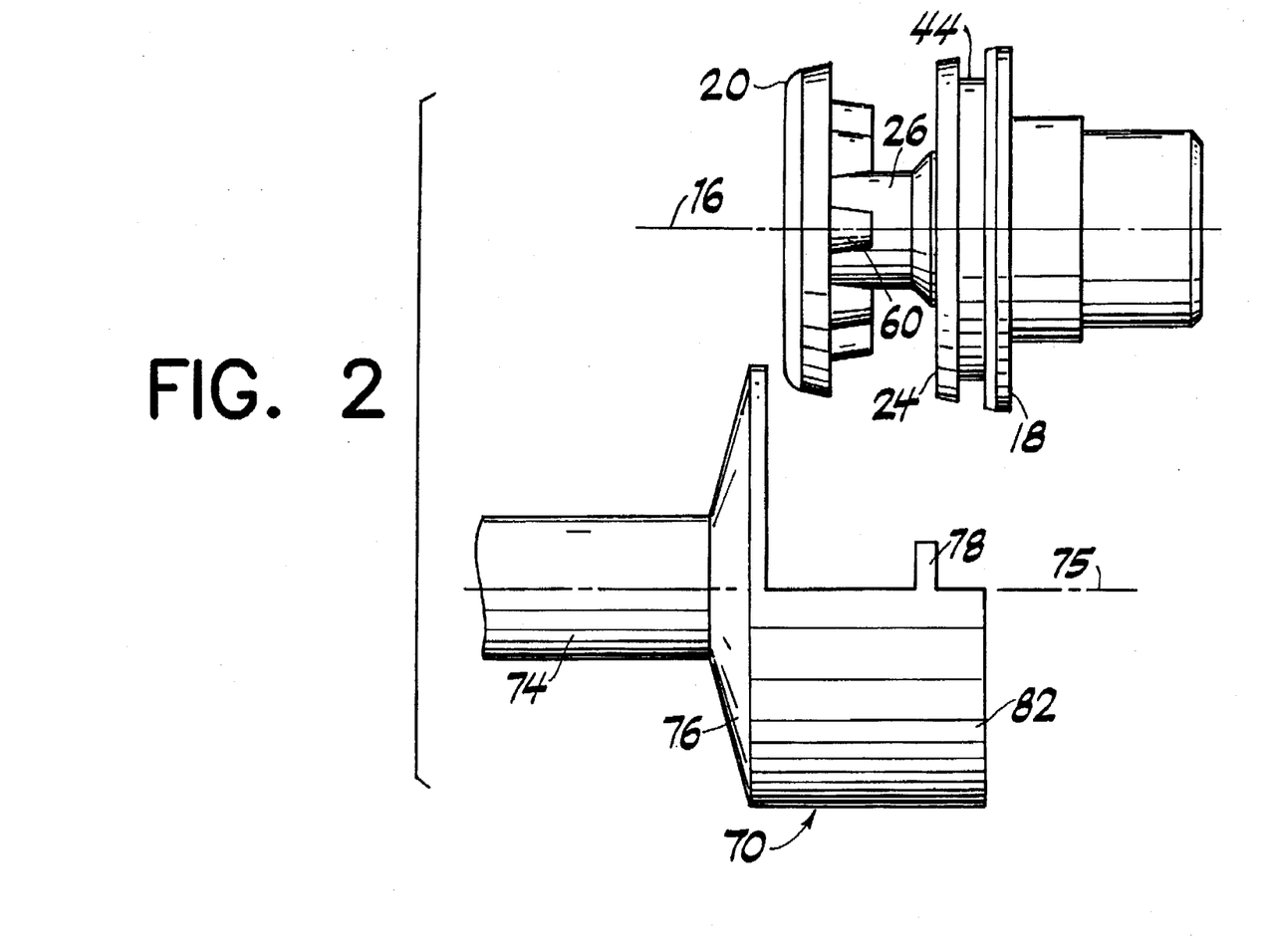
FIG. 2 is an exploded view of the components of FIG. 1 in disassembled condition.
Figure 3:
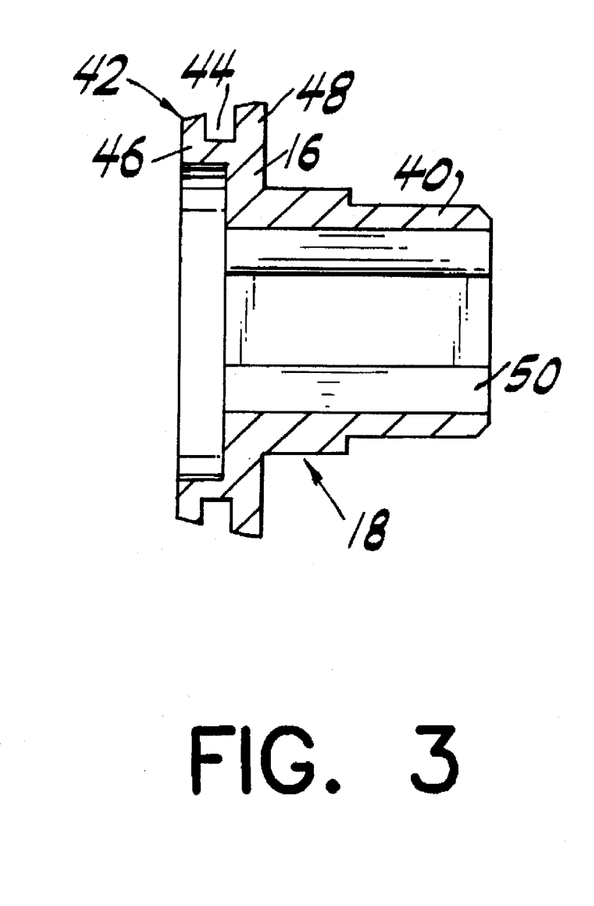
FIG. 3 is a side elevation view in cross-section of the anchor sleeve portion of FIG. 2.
Figure 4:
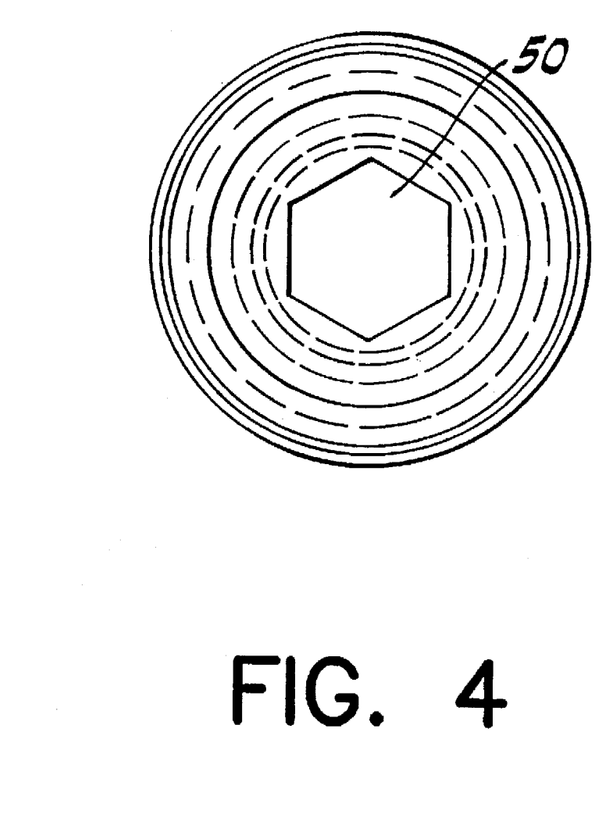
FIG. 4 is a left side view of FIG. 5.
Figure 5:
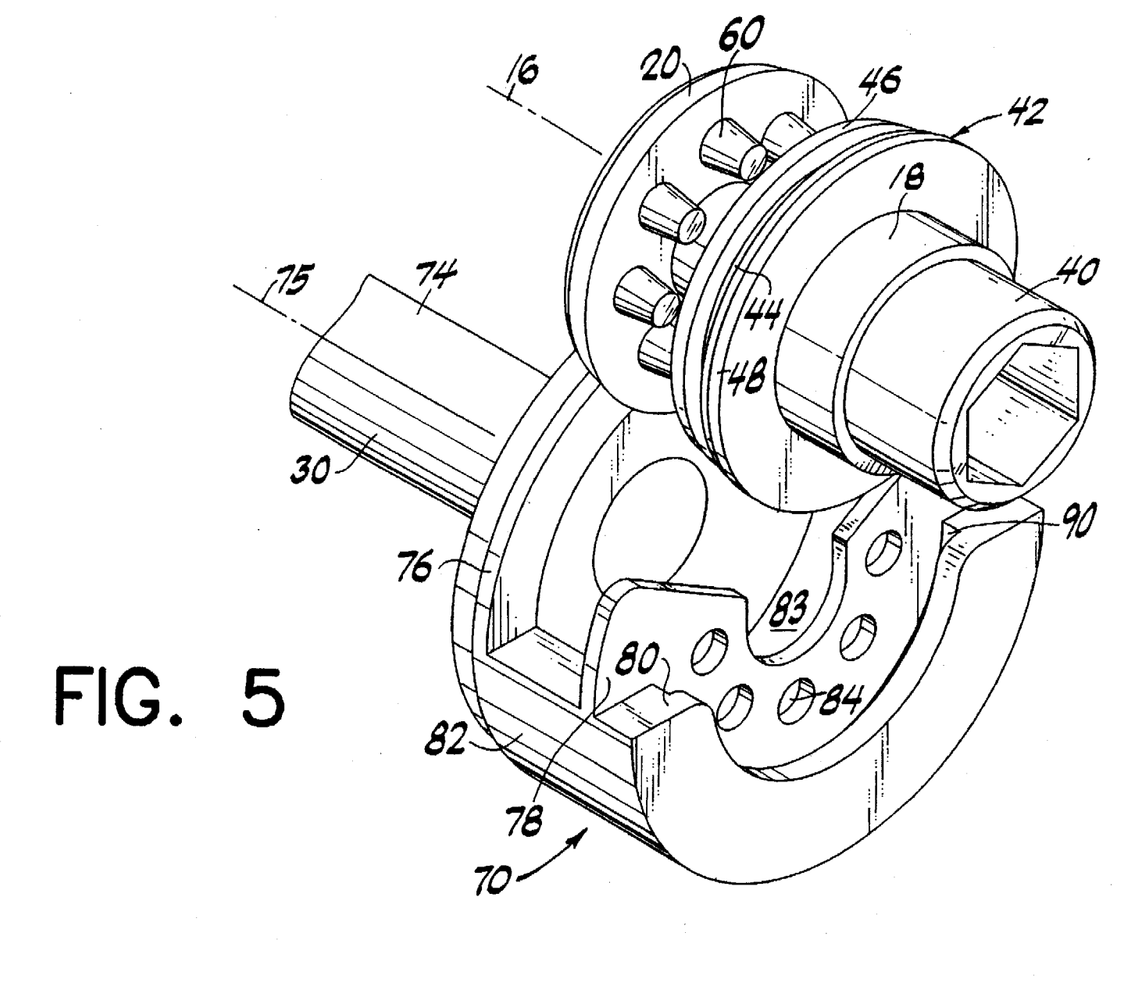
FIG. 5 is a rear perspective view of FIG. 2.

Collet mechanism 10 comprises an annular anchor sleeve 18 and a clamping head 20 secured by a shaft 22 to the body of the handpiece. Sleeve 18 is attached so as to be movable relative to the handpiece and the clamping head is movable relative to the sleeve. Shaft 22 has a proximal portion 24 and a distal portion 26 and is adapted to be longitudinally slidable along axis 16 relative to anchor sleeve 18 and driven in an oscillating manner with sleeve 18 in a plane transverse to axis 16. Distal portion 26 adjacent clamping head 20 has a circular cross-section while proximal portion 24 has a hexagonal cross-section. Anchor sleeve 18 has a cylindrical body portion 40 at its proximal end and a head portion 42 at its distal end. Head portion 42 has an annular anchoring groove 44 bounded by distal and proximal flanges 46 and 48, respectively. Sleeve 18 is provided with an axial bore 50 having a hexagonal cross-section adapted to slidingly mate with proximal shaft portion 24.

Figure 7:
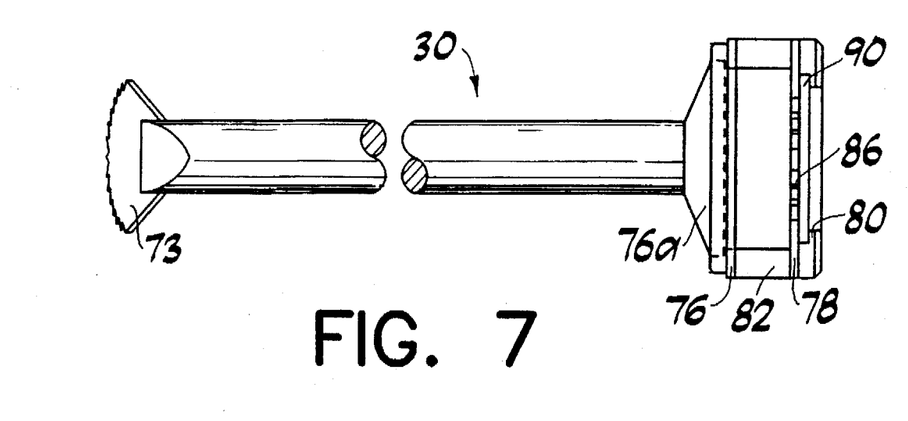
FIG. 7 is a top plan view of FIG. 6.
Figure 8:
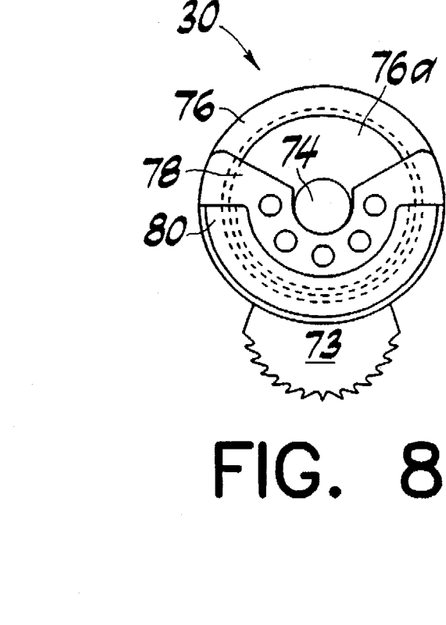
FIG. 8 is a right side view of FIG. 6.

Collet mechanism 10 is adapted to engage a flat blade in a conventional manner such that the blade will extend and oscillate in a plane perpendicular to axis 16. The collet will also receive an axially elongated angled blade 30 (best seen in FIGS. 6, 7 and 8) or crescentic blade 31 (best seen in FIGS. 9, 10 and 11) as will be explained below. Clamping head 20 is provided with a plurality of longitudinally extending pins 60 adapted to engage corresponding apertures in a blade hub. A spring mechanism (not shown) is used to bias head 20 to either an open or closed position. Sleeve 18 has a distally facing annular base surface 24 against which clamping head 20 presses a portion of the blade hub. The annular structure of collet 10 and the arcuate structure of the blade hub enable the blade to be assembled with the handpiece on any side of the handpiece axis.

Blades 30 and 31 each have essentially the same hub configuration since they are each adapted to mate with collet 10. Blade 30, as shown in FIGS. 5 through 8, has a proximal hub end 70, a distal end 72 with an angled cutting surface 73 and an elongated body 74 extending therebetween. The axis 75 of the elongated body 74 is the axis of blade 30 and is aligned with axis 16 when the blade is assembled with the collet. As used herein, the term "blade axis" refers to the axis about which a blade is oscillated which, in the case of blade 30 is axis 75. The blade axis of a crescentic blade is also the axis of the collet to which it is attached since the body of such a blade has a radius of curvature centered on this axis. Proximal end 70 is provided with an integral hub having a distally situated circular ring portion 76, an intermediate semi-circular locking flange 78 and a semi-circular proximal anchor flange 80. All of these hub parts are longitudinally spaced from each other and joined together via an off-axis cylindrical wall 82 extending parallel to the axis of the blade. Wall 82 is situated off-axis and subtends a predetermined arcuate distance to produce the open area 83 bounded by it, portion 76 and flange 78. The open area receives a part of shaft portion 26 when the blade is assembled with the collet.

Figure 6:
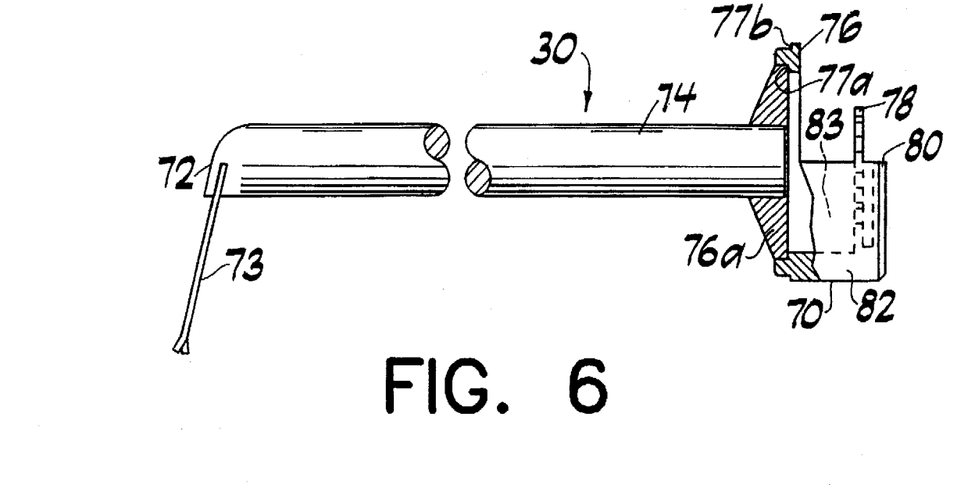
FIG. 6 is a side elevation view, partly in cross-section of the embodiment of a surgical blade shown in FIG. 1 and constructed in accordance with the principles of this invention.
Figure 9:
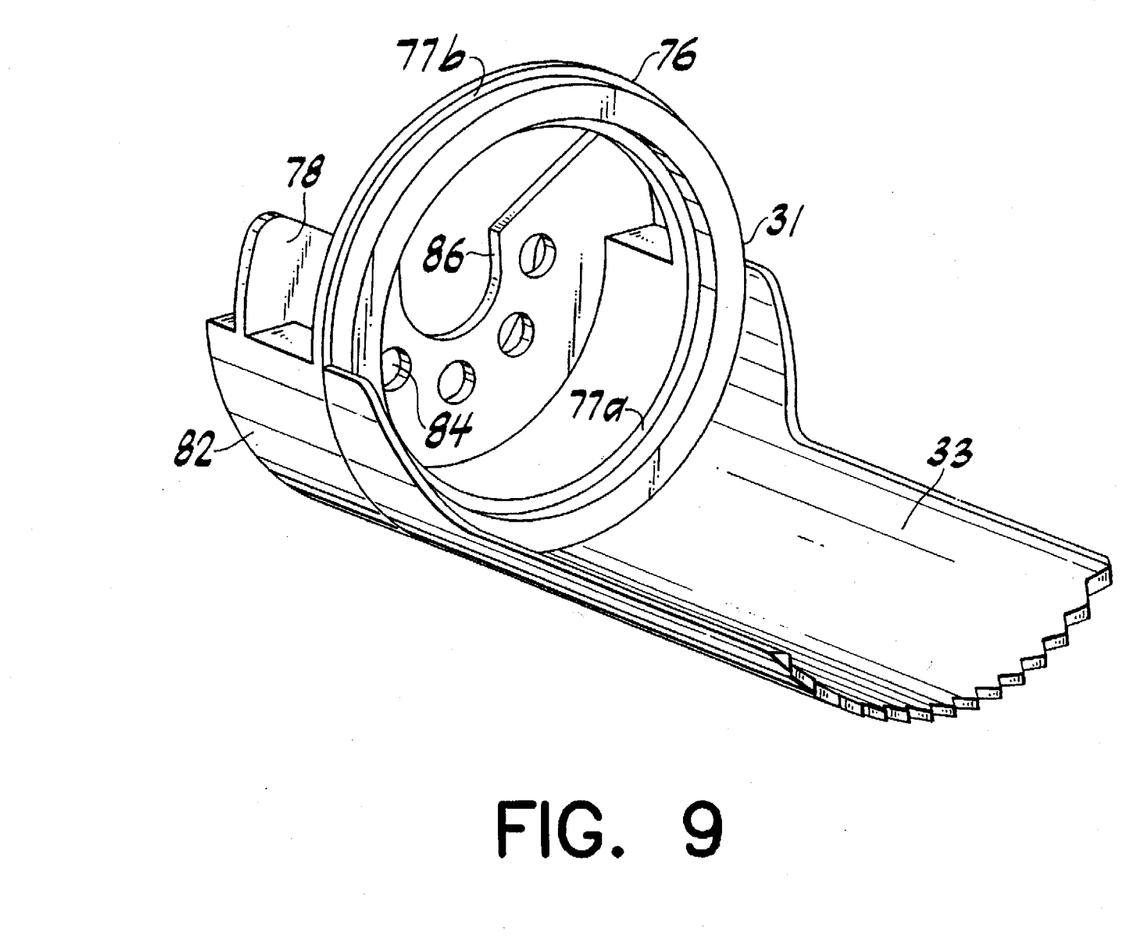
FIG. 9 is a front perspective view of another embodiment of a surgical blade constructed in accordance with the principles of this invention.
Figure 10:
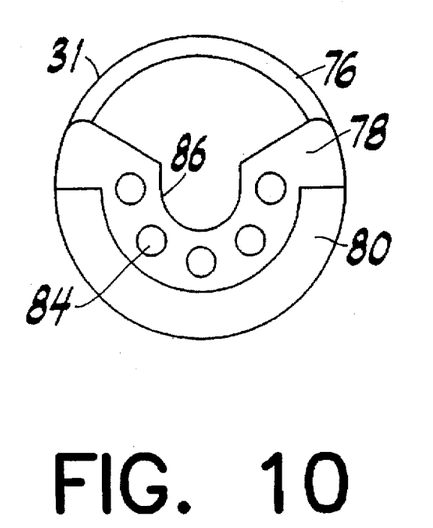
FIG. 10 is an elevation view of the proximal end of a blade hub portion of the invention.
Figure 11:
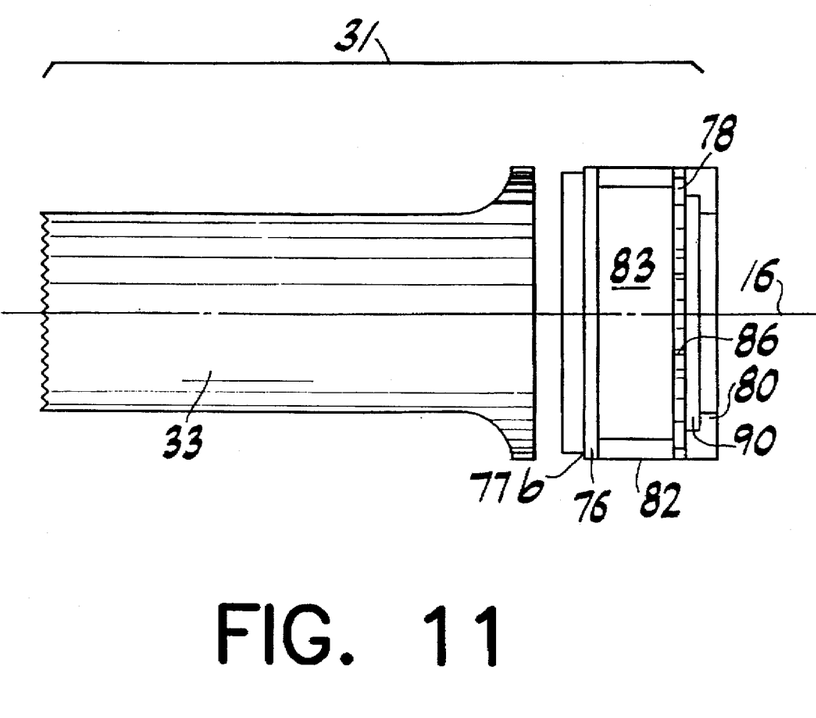
FIG. 11 is a top plan view of FIG. 7 showing a crescentic blade body attached to the hub.

In the preferred embodiment, a common distal hub portion 76 is adaptable to either a crescentric blade 31 (as best seen in FIG. 9) or angled blade 30 (as best seen in FIG. 6). Only the structures on the distally facing side of portion 76 vary between these blades. In the case of angled blade 30, the proximal end of shaft 74 is welded to a base 76a which is welded to an inside shoulder 77a of ring portion 76 (FIG. 6). In the case of crescentic blade 31, the proximal end of curved body 33 is welded to an outside shoulder 77b of ring portion 76 (FIGS. 9 and 11). The hub structure on the proximal side of portion 76 is the same for both types of blades. Also, since the hub is designed to enable engagement of the blade with a collet having a clamping head supported by an axially aligned shaft, all flange components of the hub proximal to portion 76 are open along one side of the blade axis. In the preferred embodiment, the arcuate distance subtended by the flanges is maximized (to 180° or more) to enhance security. Intermediate flange 78 has a plurality of arcuately arranged apertures 84 sized to mate with pins 60. The radially innermost edge of flange 78 has an arcuate surface 86 adapted to closely approximate the adjacent portion of shaft 22 when the hub is assembled with the collet. While the preferred embodiment is shown with arcuate flanges on the hub and circular flanges on the collet, it will be understood that other shapes may be utilized while still achieving an interdigitating type of action.

It will be understood that when collet mechanism 10 is in the open position as shown in FIG. 2, the flanges of blade hub 70 may be mated with the collet in an interlocking manner by placing anchor flange 80 into anchoring groove 44 and clamping head 20 into the space 83 bounded by cylindrical wall 82, proximal hub portion 76 and intermediate flange 78. It will be understood that gap 90 between the intermediate and proximal hub flanges 78 and 80 is sized to accommodate the thickness of distal flange 46 of the anchor sleeve. When collet 10 is then placed in a closed position (by means not shown), clamping head 20 will be urged proximally (to the right as shown in FIG. 1) by a spring (not shown) to engage pins 60 with apertures 84 and urge the proximally facing side of flange 78 against the adjacent part of base surface 24. It will be understood that any tendency of hub 70 to rock transversely within collet 10 will be resisted by the engagement between hub flanges 78 and 80 and flanges 46 and 48 on anchor sleeve 18. Indeed, the invention is also suitable for use with flat blades extending perpendicular to the handpiece axis or with rotary tools such as drills designed for non-cyclical rotation.

It will be understood that numerous other modifications and improvements may be made to the preferred embodiment of the invention disclosed herein without departing from the spirit and scope thereof.

What is claimed is:

1. A system for securing an elongated surgical device to a handpiece for driving the device, said device having an axis, a proximal end and a distal end, and said handpiece having a spring-loaded collet for receiving the proximal end of said device, said collet movable between an open position in which said device may be engaged with said collet and a closed position in which said device may be held by said collet, said system comprising:
    a hub attached to the proximal end of said device, said hub comprising:
        a first arcuate flange transverse to said axis and subtending a first predetermined arcuate distance;
        a second arcuate flange parallel to said first arcuate flange and subtending a second predetermined arcuate distance; and
    a collet means attached to said collet and said handpiece for receiving said hub, said collet means comprising:
        a first flange retaining means adapted to mate with said first arcuate flange;
        a second flange retaining means adapted to mate with said second arcuate flange.

2. A system according to claim 1 wherein said first arcuate flange subtends an arcuate distance of approximately 180°.

3. A system according to claim 1 wherein said second arcuate flange subtends an arcuate distance of approximately 180°.

4. A system according to claim 1 wherein said first flange retaining means subtends an arcuate distance greater than that of said first arcuate flange.

5. A system according to claim 1 wherein said second flange retaining means subtends an arcuate distance greater than that of said second arcuate flange.

6. A system according to claim 4 wherein said first flange retaining means subtends an arcuate distance of 360°.

7. A system according to claim 5 wherein said second flange retaining means subtends an arcuate distance of 360°.

8. A system according to claim 1 further comprising:
    an axially aligned shaft supporting said second flange retaining means; and
    an axially aligned opening in said second arcuate flange adapted to receive said axially aligned shaft;
    a plurality of annularly arranged pins longitudinally extending from said second flange retaining means; and
    a plurality of annularly arranged apertures in said second arcuate flange adapted to receive therein corresponding ones of said annularly arranged pins.

9. A system according to claim 1 further comprising:
    an off-axis wall means for joining said proximal end of said device to said first and second arcuate flanges, said off-axis wall means extending parallel to said axis at a predetermined radial distance therefrom.

10. An elongated surgical blade for use with a handpiece for driving the blade in a cyclical manner relative to the axis of the handpiece comprising:
    an elongated member having a proximal end and a distal end;
    a cutting member situated at said distal end of said elongated member;

a hub situated at said proximal end of said elongated member, said hub comprising:
   a pair of flanges transversely oriented to said axis and spaced apart from each other, said flanges adapted to engage said handpiece.

11. An elongated surgical blade according to claim 10 wherein said hub and said elongated member are unitary and wherein said cutting member is a crescentic blade.

12. An elongated surgical blade according to claim 10 wherein said elongated member is a shaft aligned parallel to the axis of said handpiece.

13. A system for securing an elongated surgical device to a handpiece for driving the device, said device having an axis, a proximal end and a distal end, and said handpiece having a spring-loaded collet for receiving the proximal end of said device, said collet movable between an open position in which said device may be engaged with said collet and a closed position in which said device may be held by said collet, said system comprising:

a hub attached to the proximal end of said device, said hub comprising:
   a first arcuate flange transverse to said axis and subtending a first predetermined arcuate distance;
   a second arcuate flange parallel to said first arcuate flange and subtending a second predetermined arcuate distance, said first and second arcuate flanges spaced a predetermined longitudinal distance; and a collet means attached to said collet and said handpiece for receiving said hub, said collet means comprising:
   a first flange retaining means adapted to mate with said first arcuate flange, said first flange retaining means longitudinally fixed relative to said handpiece and comprising an annular groove transverse to said axis;
   a second flange retaining means adapted to mate with said second arcuate flange, said second flange retaining means longitudinally movable relative to said handpiece and comprising an annular clamp surface, said clamp surface movable between an open position, in which it is spaced from said handpiece, and a closed position, in which it is adjacent said handpiece.

14. A method of attaching a surgical device to a handpiece having a spring-loaded collet movable between open and closed positions comprising the steps of:

providing the surgical device with a hub means for attaching said device to the handpiece, said hub means comprising:
   a first arcuate flange transverse to said axis and subtending a first predetermined arcuate distance;
   a second arcuate flange parallel to said first arcuate flange, transverse to said axis and subtending a second predetermined arcuate distance; and providing the handpiece and spring-loaded collet with structure adapted to hold said device, said structure comprising:
   a first flange retaining means adapted to mate with said first arcuate flange; and
   a second flange retaining means adapted to mate with said second arcuate flange;

placing said first arcuate flange adjacent said first flange retaining means and said second arcuate flange adjacent said second flange retaining means.

15. A method of supporting a surgical device on a handpiece, said device having a hub means for attaching the device to the handpiece and said handpiece having a collet means for engaging said hub, said collet means having an axis, comprising the steps of:

providing on said hub means a first plurality of apart axially spaced surfaces;

providing on said collet means a second plurality of apart axially spaced surfaces, said first and second pluralities of surfaces adapted to engage when said device is engaged with said handpiece;

interdigitating said first and second pluralities of surfaces.

\* \* \* \* \*

UNITED STATES PATENT AND TRADEMARK OFFICE
CERTIFICATE OF CORRECTION

PATENT NO. : 5,676,680
DATED : October 14, 1997
INVENTOR(S) : Joepert Lim

It is certified that error appears in the above-identified patent and that said Letters Patent is hereby corrected as shown below:

Column 8, line 30, delete "apart" and insert -- spaced --.

Column 8, line 32, delete "apart" and insert -- spaced --.

Signed and Sealed this

Third Day of February, 1998

*Attest:*

BRUCE LEHMAN

*Attesting Officer*   Commissioner of Patents and Trademarks